United States Patent
Coals et al.

(10) Patent No.: US 12,208,182 B2
(45) Date of Patent: Jan. 28, 2025

(54) DEVICE FOR DISPENSING A VOLATILE LIQUID

(71) Applicant: SCENTSTICKS LIMITED, Warminster (GB)

(72) Inventors: Stephen Richard Coals, Seaford (GB); Terence Man Wai Ng, Hong Kong (CN)

(73) Assignee: SCENTSTICKS LIMITED, Warminster (GB)

( * ) Notice: Subject to any disclaimer, the term of this patent is extended or adjusted under 35 U.S.C. 154(b) by 1030 days.

(21) Appl. No.: 17/046,102

(22) PCT Filed: Apr. 10, 2019

(86) PCT No.: PCT/GB2019/051036
§ 371 (c)(1),
(2) Date: Oct. 8, 2020

(87) PCT Pub. No.: WO2019/197824
PCT Pub. Date: Oct. 17, 2019

(65) Prior Publication Data
US 2021/0030913 A1 Feb. 4, 2021

(30) Foreign Application Priority Data
Apr. 10, 2018 (GB) ..................... 1805903

(51) Int. Cl.
*A61L 9/12* (2006.01)
*A01M 1/20* (2006.01)
*A61L 9/04* (2006.01)

(52) U.S. Cl.
CPC ........... *A61L 9/127* (2013.01); *A01M 1/2044* (2013.01); *A61L 9/046* (2013.01)

(58) Field of Classification Search
CPC ...................................................... A61L 9/127
See application file for complete search history.

(56) References Cited

U.S. PATENT DOCUMENTS

| | | |
|---|---|---|
| 2,629,149 A | 2/1953 | Yaffe |
| 3,953,378 A | 4/1976 | Lasser |
| 4,285,905 A | 8/1981 | Feit |
| 5,919,516 A | 7/1999 | Hsieh |

(Continued)

FOREIGN PATENT DOCUMENTS

| | | |
|---|---|---|
| CN | 103536175 A | 1/2014 |
| CN | 106106448 A | 11/2016 |

(Continued)

OTHER PUBLICATIONS

Chinese Office Action mailed Jan. 5, 2022 in related Chinese Application No. 201980024998.X, 18 pages.

*Primary Examiner* — Kevin Joyner
*Assistant Examiner* — Changru Chen
(74) *Attorney, Agent, or Firm* — Fox Rothschild LLP

(57) ABSTRACT

The present invention relates to a device for dispersing a volatile liquid comprising: a wick; a solid support; and a volatile liquid; wherein the wick is attached to the solid support; wherein the solid support is porous; and wherein the volatile liquid is contained within pores in the solid support. The invention also relates to methods of making such a device.

18 Claims, 4 Drawing Sheets

(56) References Cited

U.S. PATENT DOCUMENTS

| | | | |
|---|---|---|---|
| 2007/0217771 A1* | 9/2007 | Granger | A01M 1/2033 |
| | | | 392/386 |
| 2009/0313865 A1 | 12/2009 | Peretti et al. | |
| 2010/0308126 A1* | 12/2010 | Gruenbacher | A61L 9/04 |
| | | | 239/6 |
| 2011/0031327 A1 | 2/2011 | Mallochet et al. | |
| 2011/0290908 A1 | 12/2011 | Tranzeat et al. | |
| 2014/0332990 A1 | 11/2014 | Brosmith | |
| 2017/0120729 A1 | 5/2017 | Rasmussen | |
| 2017/0360980 A1 | 12/2017 | Jakins et al. | |

FOREIGN PATENT DOCUMENTS

| | | | | |
|---|---|---|---|---|
| GB | 2194148 A * | 3/1988 | | A61L 9/127 |
| WO | WO-2010077942 A1 * | 7/2010 | | A61L 9/127 |
| WO | 2013/025585 A1 | 2/2013 | | |
| WO | 2016/053802 A1 | 4/2016 | | |
| WO | 2016/184809 A1 | 11/2016 | | |

* cited by examiner

DEVICE FOR DISPENSING A VOLATILE LIQUID

FIELD OF THE INVENTION

The invention relates to a device for dispensing a volatile liquid into the surrounding atmosphere, and a method for making said device.

BACKGROUND OF THE INVENTION

Devices for dispensing volatile liquids, such as fragrances or perfumes, are used everyday by consumers looking to dispense fragrances or perfumes to mask or neutralize unpleasant odours, or to simply provide a pleasant scent in the surroundings of the device, for example in a bathroom or living room. Such devices are not limited to dispensing fragrances or perfumes, and can readily be adapted to dispense volatile liquids having some other beneficial property, for example insect repellents.

Various types of devices for dispensing volatile liquids, such as fragrances, perfumes and insect repellents, have been made. For example, one known type of device simply comprises a carrier, such as plaster of Paris, into which a volatile liquid, such as a perfume, has been incorporated. This type of solid device can be prepared simply by mixing a volatile liquid with powdered plaster of Paris and water, pouring the mixture into a mould, and allowing the mixture to harden. The volatile liquid is gradually released from the device once formed.

Such devices are known from U.S. Pat. No. 3,953,378, which discloses a process for preparing a gypsum article containing a volatile substance.

Devices which simply comprise a carrier and a volatile liquid are easy to manufacture, and can in fact be made individually by a user at home with easily obtainable materials. In addition, the devices can be made into any shape, since the shape of the device is determined by the shape of the mould.

However, one disadvantage of such devices is that the strength of the commonly used carriers (e.g. plaster of Paris) is relatively low, meaning that they are easy to break.

Another type of device which is used for dispensing volatile liquids is a wick or reed based device, commonly called a reed diffuser. Wick or reed based devices generally comprise a reservoir of volatile liquid, and a porous wick or reed which is partially immersed in said liquid, and partially exposed to the atmosphere. The volatile liquid soaks into the immersed part of the porous wick or reed, then travels along the wick or reed through capillary action. The volatile liquid then dispenses by evaporation from the exposed surface of the wick or reed into the surrounding atmosphere.

Such devices are known from U.S. Pat. No. 8,882,998, which discloses a wick based device comprising a reservoir of volatile substance and at least one wick member which is formed from a porous material capable of being impregnated with a volatile substance.

One problem with wick based devices, such as those known from U.S. Pat. No. 8,882,998, is that they are relatively bulky, due to the need for a reservoir of liquid. In addition, these devices can be messy, since they require the user to periodically top up the reservoir with a volatile liquid (e.g. fragrance or perfume). Similarly, due to the need for a liquid reservoir the devices are not easy to transport, and must generally be left in a single location.

Furthermore, due to the need for a reservoir containing a liquid, it is difficult to form these devices into any shape, or to suspend them (e.g. from a hook) above the ground. Rather, known reed diffuser devices are generally required to remain on a flat surface, and must contain wicks or reeds which are long and thin, such that they can be partially immersed in the liquid and partially exposed to the atmosphere.

The device of the present invention is an amalgamation of the wick based and solid devices discussed above, which overcomes the deficiencies of both.

SUMMARY OF THE INVENTION

The device of the present invention acts to dispense a volatile liquid into the atmosphere. For example, the device may be used in a user's home, in particular a living room or bathroom, to dispense a fragrance or perfume. Alternatively, the device may be used to dispense an insect repellent, in which case it may be desirable to use the device outside or in a bedroom.

In one aspect, the present invention provides a device for dispensing a volatile liquid into the surrounding atmosphere comprising:
  a wick;
  a solid support; and
  a volatile liquid;
  wherein the wick is attached to the solid support;
  wherein the solid support is porous; and
  wherein the volatile liquid is contained within pores in the solid support.

In another aspect, the present invention provides the device described above which is sealed in airtight packaging.

In another aspect, the present invention provides a method for producing the device of the invention, said method comprising:
  (a) mixing a solid support precursor and water to form a slurry;
  (b) contacting a wick with the slurry in a mould;
  (c) drying the slurry to form the device;
  wherein the slurry formed in step (a) also comprises a volatile liquid.

The wick may also be porous, in which case step (b) may comprise applying a volatile liquid to a porous wick before contacting the wick with the slurry.

In another aspect, the present invention provides devices produced by the method set out above.

The device of the invention is a simple, easy to use and portable device that can be used to dispense a volatile liquid, such as a fragrance, wherever and whenever it is required. As with known reed diffuser devices, the device of the present invention provides for enhanced dispensing of a volatile liquid into the atmosphere. However, unlike reed diffuser devices, the device of the present invention is not bulky, and does not require a reservoir of volatile liquid to be constantly topped up. In addition, the device of the present invention can easily be shaped or formed into any suitable shape, and can be placed on a surface or suspended from a support (e.g. a hook). As it can be easily shaped, the device of the invention may also be used as a decoration.

The device of the present invention should be contained in airtight packaging for storage and/or transport. To activate the device it is simply removed from the air tight packaging, after which the volatile liquid will start to evaporate into the surrounding atmosphere.

LIST OF FIGURES

DETAILED DESCRIPTION OF THE INVENTION

Wick

Figure 1:
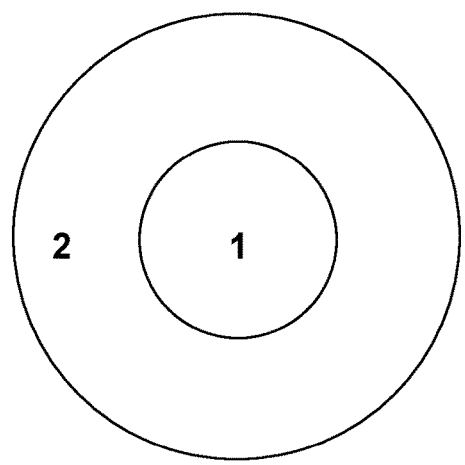
FIG. 1 is a schematic illustration of a cross section of a device of the invention.

As used herein, the term "wick" also includes a "reed", a "rod", a "tube", a "wire", a "bar" or the like, of any material that can provide strength and flexibility to the solid support. Thus, any reference to a "wick" herein should also be considered to be a reference to a "reed", a "rod", a "tube", a "wire" or a "bar". In one aspect, the wick or reed may be a wick or reed as used in a conventional reed diffuser device. The person skilled in the art would therefore be aware of suitable wicks or reeds which could be used in the present invention.

The device of the invention may comprise a single wick, or may comprise multiple wicks. If multiple wicks are present, these may be in contact with and joined to each other, or may be separate and joined by the solid support. Although only one wick is discussed herein, the device of the invention may comprise multiple wicks each having some or all of the features discussed below.

Preferably, the device of the invention comprises multiple wicks (i.e. two or more wicks). Preferably, the device comprises two, three or four wicks, more preferably two or three wicks.

In the device of the present invention, the wick is attached to the solid support, and provides strength and flexibility to the solid support. The device of the present invention is therefore stronger and more flexible than an otherwise identical device absent the wick. This means that the device of the present invention is less likely to break during transport or when in use compared to devices which comprise a solid support (e.g. gypsum) but no wick. For the same reason, the device of the present invention is portable, whereas devices known in the art are either not portable or are too fragile to be easily portable.

The wick used in the present invention is preferably porous, thereby allowing the volatile liquid to diffuse through the wick. Thus, the wick is preferably capable of being impregnated with a volatile liquid, and allowing evaporation of said volatile liquid into the device's surroundings. The wick may therefore comprise any porous material which is permeable to the volatile liquid.

Preferably, the wick acts as a reservoir which is capable of storing the volatile liquid.

Alternatively, the wick may be non-porous, and may comprise any material that can provide strength and flexibility to the solid support.

The wick may be formed of any suitable material, including metals such as copper, iron, zinc, aluminium, nickel, titanium, or combinations thereof; metal alloys, such as steel (including stainless steel and galvanised steel); plastics such as polyethylene, polypropylene, polyurethane, polystyrene, polyesters, polyvinyl chloride, polycarbonate, acrylonitrile butadiene styrene, or combinations or copolymers thereof; wax; wood or other cellulose derivatives such as bamboo or paper; fibrous materials such as jute, cotton and wool; sponge; foam rubber; pumice; larva rock; charcoal; felt; and combinations thereof.

Preferably, the wick is formed of metals such as copper, iron, zinc, aluminium, nickel, titanium, or combinations thereof; metal alloys such as steel (including stainless steel and galvanised steel); plastics such as polyethylene, polypropylene, polyurethane, polystyrene, polyesters, polyvinyl chloride, polycarbonate, acrylonitrile butadiene styrene, or combinations or copolymers thereof; wax; wood or other cellulose derivatives such as bamboo or paper; or combinations thereof.

When the wick is formed of wax, the wick may comprise a wax candle.

A preferred metal for use in the invention is aluminium. A preferred metal alloy for use in the invention is galvanised steel.

Alternatively, the wick is formed of polyester, polyethylene, cotton, sponge, foam rubber, pumice, larva rock, charcoal, felt, wood or other cellulose derivatives such as bamboo or paper, or combinations thereof.

In order to allow the device of the present invention to be environmentally friendly, it is preferred that the wick is a biodegradable material, more preferably a porous biodegradable material. The person skilled in the art would be aware of suitable biodegradable materials.

Suitable porous biodegradable materials include inorganic or organic materials, although organic materials are preferred. Examples of suitable organic porous biodegradable materials include felt, cotton, wood or other cellulose derivatives and combinations thereof. Preferred organic porous biodegradable materials include wood or other cellulose derivatives such as paper or bamboo. Preferred woods include rattan.

Thus, the wick is preferably formed of felt, cotton, wood or other cellulose derivatives, or combinations thereof. More preferably, the wick is formed of felt, cotton, wood, bamboo, or combinations thereof, even more preferably bamboo, rattan or combinations thereof, and most preferably bamboo.

Alternatively, in order to allow the device of the present invention to be environmentally friendly, the wick may be a material which is readily recyclable, such as a metal.

The wick used in the present invention may be any shape, and thus can be a simple shape or can form a complex intricate design. Suitable simple shapes include a cube, a cuboid, a cylinder or an ovoid. Preferably, the wick is cylindrical.

The wick may be straight (e.g. to form a cuboid, cylinder etc.) or bent (e.g. to form a design or pattern). For example, the wick may form a torus shape, wherein the cross-section of the wick is circular, and the wick is bent into a circle along its length. Alternatively, the wick may form a heart shape having any suitable cross-sectional shape. Alternatively, the wick may be in the form of a mesh.

The wick may have a cross-section (when taken perpendicular to the length of the wick) that is rectangular, square, ovoid or circular, preferably ovoid or circular. The length of the wick is defined as the distance between one end of the wick and the other, following any bends. For example, the length of a wick which is bent into a torus shape is the circumference of the torus.

The wick may be of any suitable size. For example, the wick may have a length of from about 1 to about 50 cm, preferably from about 5 to about 40 cm, more preferably from about 10 to about 30 cm, and most preferably from about 20 to about 25 cm.

Preferably, the thickness (the smallest dimension) of the wick is from 0.5 mm to 15 mm, more preferably from about 1 mm to about 10 mm, more preferably from about 2 mm to about 8 mm, and most preferably from about 3 mm to about 5 mm.

For example, if the wick is a cylinder, it is preferred that the diameter of the cylinder ranges from about 0.5 mm to about 15 mm, more preferably from about 1 mm to about 10 mm, more preferably from about 2 mm to about 8 mm, and most preferably from about 3 mm to about 5 mm. Similarly, it is preferred that the length of the cylinder ranges from about 20 to about 25 cm.

If the device comprises more than one wick, each wick may be the same shape and/or size, or may be a different shape and/or size. In one embodiment, each wick is the same size and shape.

Where two or more wicks are present, the thickness of each wick may be narrower. Thus, in this case the thickness (e.g. diameter) of each wick may be from about 0.5 to about 8 mm, more preferably from about 1 mm to about 5 mm, more preferably from about 1 mm to about 3 mm.

As discussed above, the wick is attached to the solid support. To provide suitable strength and flexibility, it is preferred that at least about 40% of the total surface of the wick is attached to the solid support. More preferably, at least about 70% of the total surface of the wick is attached to the solid support. Most preferably, at least about 90% of the total surface of the wick is attached to the solid support.

Preferably, the wick comprises from about 1 to about 50 vol. % of the device, such as from about 5 to about 50 vol. % of the device. More preferably, the wick comprises from about 10 to about 30 vol. % of the device.

Alternatively, the wick comprises from about 1 to about 5 vol. % of the device, such as from about 2 to about 4 vol. % of the device.

Solid Support

The solid support is attached to the wick, and provides the wick with support, since the wick itself may not be strong enough to be used in a device alone.

The solid support used in the present invention is porous. Thus, the solid support may comprise any porous material which is permeable to the volatile liquid. The volatile liquid can therefore diffuse through the solid support and evaporate from the surface of said support. As such, the solid support acts as a reservoir which is capable of storing the volatile liquid.

For example, the solid support may comprise a porous inorganic material, such as a porous porcelain material, a porous ceramic material or porous plaster. Alternatively, the solid support may comprise a porous organic material such as a porous polymer, preferably a porous biodegradable polymer.

Suitable porous polymers would be known to those skilled in the art, and include porous polyamides, for example porous nylon, and porous polyesters, for example porous polylactic acid.

Alternatively, if a glue or adhesive is present in the solid support, then the solid support may comprise powdered chalk, powdered lime, soy powder, flour, paper pulp, wood powder or combinations thereof, in combination with a glue or adhesive.

Preferably, the solid support comprises a porous plaster, more preferably gypsum plaster (plaster of Paris).

The grade of plaster is preferably selected from alpha or beta grade, or combinations thereof.

Preferably, the solid support comprises a material which is biodegradable or recyclable. Since plaster is easily recyclable (e.g. by grinding and heating the used plaster), when the solid support comprises a porous plaster the device of the present invention is more environmentally friendly, since the solid support can be recycled. Similarly, if the solid support is biodegradable the device is also more environmentally friendly. When the solid support is recyclable or biodegradable and the wick is biodegradable the device of the invention is highly environmentally friendly.

Since the shape of the solid support is determined by the mould in which it is set, the shape of the solid support can be any shape that can be moulded. For example, the solid support may form a polyhedron such as a sphere or a cuboid, or may form a cylinder or an ovoid. Other more complex shapes can also be produced, such as a fluted shape (e.g. a fluted column), or the shape of a tree trunk. Preferably, the solid support is a cylinder.

As discussed above, the solid support is attached to the wick, and provides the wick with support. To provide the device with suitable strength and flexibility, it is preferred that the solid support at least partially encapsulates the wick. Alternatively, the solid support may completely encapsulate the wick.

Thus, the solid support preferably comprises a coating on the wick. In this case the solid support can be any shape which partially or fully encapsulates the wick. Thus, the coating can partially or fully encapsulate the wick.

Figure 2:
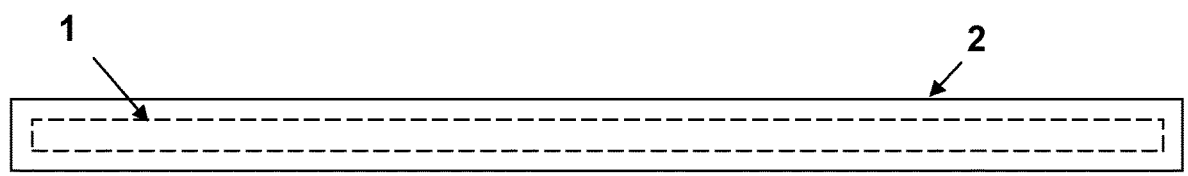
FIG. 2 is a schematic illustration of a side-on view of the device of FIG. 1.

For example, FIG. 1 shows the cross section of a device wherein the wick (1) is a cylinder which is completely encapsulated by the solid support (2). FIG. 2 shows a side-on view of the same device, with the encapsulated (and therefore hidden) wick (1) shown in dashed lines.

Figure 3:
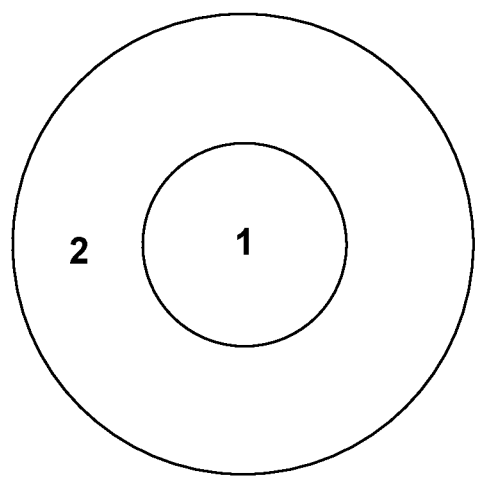
FIG. 3 is a schematic illustration of a cross section of a device of the invention.
Figure 4:
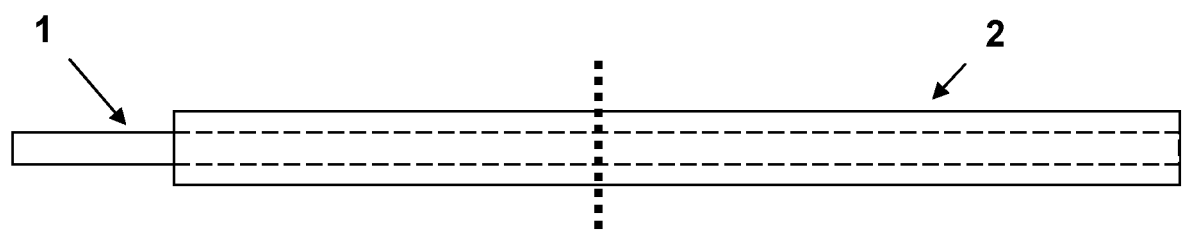
FIG. 4 is a schematic illustration of a side-on view of the device of FIG. 3.

An alternative embodiment is shown in FIGS. 3 and 4, where the solid support (2) forms an incomplete coating on the cylindrical wick (1). FIG. 3 shows a cross-section of the device of FIG. 4 taken at the dotted line.

Figure 5:
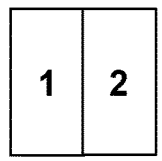
FIG. 5 is a schematic illustration of a cross section of a device of the invention.
Figure 6:
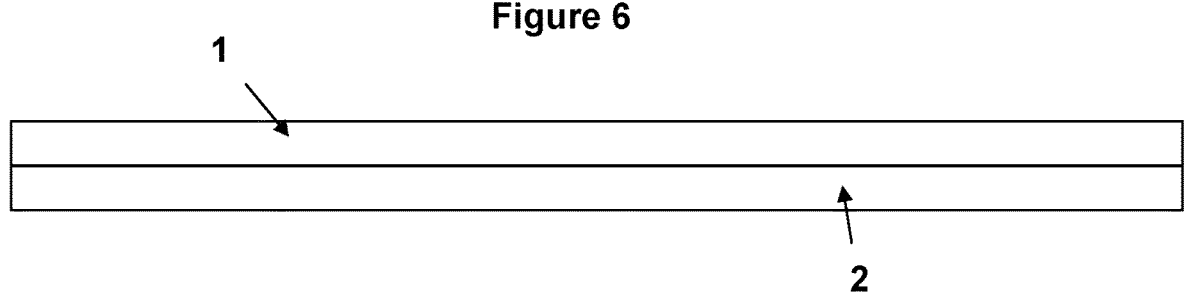
FIG. 6 is a schematic illustration of a side-on view of the device of FIG. 5.

FIGS. 5 and 6 show an embodiment where the wick is attached to the solid support, but the solid support does not encapsulate the wick. For example, FIG. 5 shows the cross section of a device wherein the wick (1) is attached to the solid support (2) but is not surrounded by said solid support (2). FIG. 6 shows a side-on view of the same device, with both the wick (1) and the solid support (2) being exposed.

Figure 7:
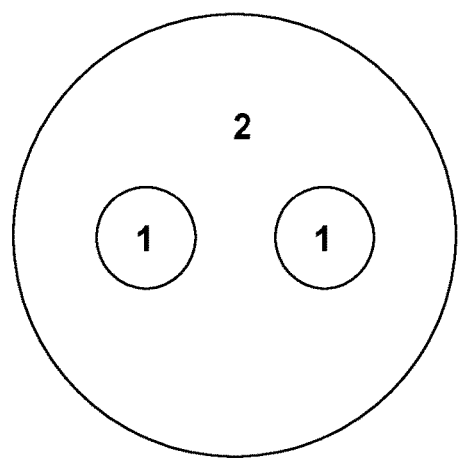
FIG. 7 is a schematic illustration of a cross section of a device of the invention comprising two wicks.
Figure 8:
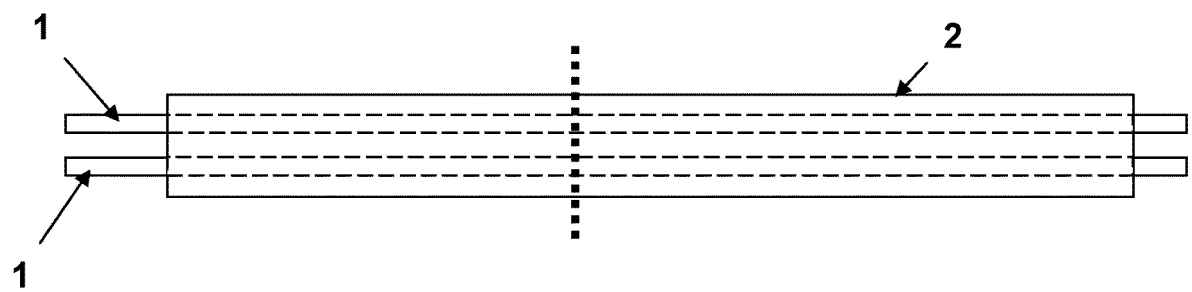
FIG. 8 is a schematic illustration of a side-on view of the device of FIG. 7.

FIGS. 7 and 8 show an embodiment where the device comprises two wicks, and wherein the solid support (2) forms a coating on a portion of the cylindrical wicks (1). Part of the wick is therefore exposed and protrudes from the solid support. FIG. 7 shows a cross-section of the device of FIG. 8 taken at the dotted line.

When the solid support at least partially encapsulates the wick it is preferred that the solid support forms a coating around the wick having a thickness of at least about 0.5 mm. Preferably, the coating has a thickness of from about 0.5 to about 10 mm, more preferably from about 1 to about 5 mm, and most preferably from about 2 to about 4 mm.

Where a portion of the wick is exposed and uncoated by the solid support, said portion can be used to hold the device. For example, if the wick comprises a hollow tube, the device could be mounted on a projection (e.g. a spike) by inserting the projection into an exposed end of the hollow tube.

The solid support may be of any suitable size. For example, the solid support may have a longest dimension of between about 1 and about 50 cm, preferably between about 5 and about 40 cm, more preferably between about 10 and about 30 cm, and most preferably between about 20 and about 25 cm.

Volatile Liquid

The device of the present invention is a device for dispensing a volatile liquid into the surrounding atmosphere. The term "dispensing" as used herein includes "dispersing" and "diffusing". Thus, by "dispensing" a volatile liquid it is meant that the volatile liquid is dispensed, dispersed or diffused in the form of a gas or vapour produced by the evapouration of the volatile liquid.

The term "volatile liquid" as used herein means a liquid that can evaporate under atmospheric pressure at room temperature (25° C.).

The evaporation rate of the volatile liquid will of course depend on the nature of the volatile liquid. In addition, the length of time over which the device is able to dispense said volatile liquid (i.e. the lifetime of the device) will depend at least in part on the evaporation rate of the volatile liquid. As such, the volatile liquid can be selected depending on the desired lifetime of the device.

Any volatile liquid may be used in the invention, provided that the liquid can impregnate and diffuse from the wick and/or solid support. Suitable volatile liquids (e.g. perfumes, fragrances, insect repellents and pheromones) are well known to the skilled person, and include those commercially available for use with conventional reed diffusers. Commercially available perfumes and fragrances include those supplied by Quintessence Fragrances.

Preferably, the volatile liquid is selected from a fragrance, a deodorizer, a sanitizer, an insect repellent, a pheromone, or combinations thereof, optionally combined with a solvent. Preferably, the volatile liquid is a fragrance, an insect repellent or a combination thereof, optionally combined with a solvent, more preferably a fragrance optionally combined with a solvent.

Any suitable solvent may be used, such as water; glycols (e.g. ethylene glycol, propylene glycol, diethylene glycol and 1,3-butylene glycol); glycol ethers (e.g. propylene glycol methyl ether, dipropylene glycol methyl ether, tripropylene glycol methyl ether, propylene glycol methyl ether acetate, dipropylene glycol methyl ether acetate, propylene glycol n-propyl ether, dipropylene glycol n-propyl ether, propylene glycol n-butyl ether, dipropylene glycol n-butyl ether, tripropylene glycol n-butyl ether, dipropylene glycol dimethyl ether, ethylene glycol n-butyl ether, diethylene glycol n-butyl ether, ethoxypropanol, methoxybutanol and methoxymethylbutanol); alcohols (e.g. ethanol, propanol, butanol, and solketal); polyols (e.g. glycerol); isoparaffins (e.g. isoparaffin C11-C14), siloxanes (e.g. cyclopentasiloxane); and combinations thereof.

Preferably, the solvent is selected from glycol ethers, alcohols, isoparaffins, siloxanes, and combinations thereof. More preferably, the solvent is selected from glycol ethers (preferably propylene glycol ethers such as dipropylene glycol methyl ether), alcohols (preferably ethanol), and combinations thereof. For example, the solvent may be selected from dipropylene glycol methyl ether and ethanol.

If present, the solvent is preferably present in the amount of from about 10 to about 90 wt. %, more preferably from about 20 to about 70 wt. %, most preferably from about 40 to about 60 wt. %, based on the total weight of the volatile liquid and the solvent.

A single volatile liquid can be used, or a mixture of volatile liquids can be used. As used herein, references to a volatile liquid include a combination of a volatile liquid and one or more solvents; or a mixture of volatile liquids, optionally including one or more solvents; or a volatile liquid formed by dissolving a solid in a solvent. For example, as used herein, the term fragrance or perfume includes a single volatile liquid having a fragrance as well as a fragrance composition formed of multiple volatile liquids, optionally in combination with a solvent. A fragrance can also comprise solids (such as menthol or camphor) dissolved in a liquid component (e.g. a solvent).

The device of the present invention is intended to be disposable, such that after all the volatile liquid has been dispensed the device is discarded and preferably recycled. In order that the user is aware when the device has reached the end of its life, if a volatile liquid having no fragrance detectable to humans (e.g. an insect repellent) is present in the device, it is preferred that a second volatile liquid having a fragrance detectable to humans is also present in the device. In this case, the two volatile liquids should be present in approximately the same amounts, such that they will both be fully dispensed at the same time.

As discussed above, the volatile liquid is contained within the solid support, and may optionally also be contained within the wick. Thus, the solid support is capable of containing the volatile liquid and acts as a reservoir for storing the volatile liquid of the device. Optionally, the wick is also capable of containing the volatile liquid and as such also acts as a reservoir for storing the volatile liquid of the device.

Where a volatile liquid is present in the wick and the solid support, the volatile liquid in the wick may differ from the volatile liquid in the solid support. For example, a fragrance may be used as a volatile liquid in the solid support, and an insect repellent or pheromone may be used as a volatile liquid in the wick (or vice versa). Alternatively, the volatile liquid may be the same in the wick and the solid support.

Where a pheromone is used in the device, the device may be used to trap insects. For example, a pheromone capable of attracting insects can be used, and the device may be at least partially coated in a coating that is sticky, such that it is capable of trapping insects which touch the device. Alternatively, the device could be placed inside a cage which is capable of trapping insects, for example inside a cage which is coated in a sticky substance. Pheromone traps such as these may be used in any setting where it is desirable to trap insects, for example to protect fruit crops or to trap clothes moths.

Preferably, the volatile liquid is contained within the solid support, and optionally the wick, in the amount of from about 5 to about 60 wt. %, based on the total weight of the device, more preferably from about 10 to about 50 wt. %, most preferably from about 20 to about 40 wt. %.

Preferably, the volatile liquid is contained within the solid support in the amount of from about 1 to about 40 wt. %, preferably about 5 to about 30 wt. %, based on the total weight of the solid support and the volatile liquid.

When the volatile liquid is also present in the wick, it is preferred that the volatile liquid is contained within the wick in the amount of from about 20 to about 60 wt. %, preferably from about 30 to about 55 wt. %, based on the total weight of the wick and the volatile liquid.

It is preferred that the volatile liquid is contained within the wick and the solid support. In this case, preferably at least about 50 wt. % of the volatile liquid present in the device (when initially formed) is contained within the solid support. More preferably, at least about 70 wt. % of the volatile liquid present in the device (when initially formed) is contained within the solid support.

Since the device of the present invention contains a volatile liquid within the solid support, or the solid support and the wick, unlike many devices known in the art the volatile liquid does not need to be supplied to the solid support, or the solid support and the wick, by means of a reservoir external to the solid support or the solid support and the wick. This is an advantageous because devices comprising such an external reservoir of volatile liquid are bulky and are prone to accidents when the reservoir is topped up.

Thus, it is preferred that the device of the invention does not comprise an external reservoir. By "external reservoir" it is meant any reservoir for storing volatile liquid that is not a wick and/or solid support of the invention. Typically, an "external reservoir" comprises a non-porous material. For example, reed diffuser devices generally comprise a bottle of fragrance, typically made of glass, which is equivalent to an "external reservoir" of fragrance. Thus, preferably the device of the invention does not comprise a bottle for storing volatile liquid.

Put another way, it is preferred that in the device of the present invention the volatile liquid is contained solely within the solid support, or the solid support and the wick, in particular within the pores of the solid support, or the pores of the solid support and the wick.

When the device of the invention is exposed to the atmosphere, over time the volatile liquid will diffuse through the wick and/or solid support and evaporate into the atmosphere. The volatile liquid will provide the desired effect (e.g. fragrance and/or insect repellence) for the user once evaporated.

When the wick is partially or fully encapsulated by the solid support, and the volatile liquid is contained within the wick and the solid support, the volatile liquid initially contained within the wick will diffuse through both the wick and solid support before evaporating from the surface of the device into the atmosphere.

Optional Components

The device of the present invention may contain optional components to improve, for example, the aesthetic of the device.

For example, the solid support may comprise a dye or pigment to impart colour to the solid support and/or wick, preferably to the solid support. If present, the dye is preferably present in the amount of from about 0.001 to about 3 wt. %, preferably from about 0.001 to about 1 wt. %, more preferably from about 0.05 to about 0.5 wt. %, based on the weight of the device.

Alternatively, or in addition, the solid support may comprise an additive selected from odour eliminators, glitters, metallic powers and suspensions, antioxidants, UV inhibitors, or combinations thereof. If present, the additive is preferably present in the amount of from about 0.001 to about 1 wt. %, more preferably from about 0.05 to about 0.5 wt. %, based on the weight of the device.

Alternatively or in addition, the device of the present invention may be entirely or partially coated with an additional outer layer. Said outer layer may be porous (e.g. a porous paint). Alternatively, said outer layer may be non-porous or impervious to liquid (e.g. a non-porous paint or glaze). In the latter case, the device can be partially coated with said outer layer, but must not be entirely coated with said outer layer.

The outer layer could act to prevent the volatile liquid from migrating from the device onto a surface on which the device is placed; to reduce the rate at which the volatile liquid is released from the device; to enable the device to float in liquid such as water; to allow the user to more easily grip the device; to prevent the device moving when placed on a surface; to trap insects; and/or for purely decorative reasons.

In the case where an outer layer is present, this may be applied to the device by any means (e.g. by dipping or spraying) after formation of the device.

Method of Making the Device

The method for making the device of the present invention comprises:
(a) mixing a solid support precursor and water to form a slurry;
(b) contacting a wick with the slurry in a mould;
(c) drying the slurry to form the device;
wherein the slurry formed in step (a) also comprises a volatile liquid.

If the wick is porous, step (b) may comprise applying a volatile liquid to the porous wick before contacting the porous wick with the slurry.

Step (a)

In step (a) a slurry comprising a solid support precursor, water and a volatile liquid is formed.

As used herein, a "solid support precursor" is a material which, when moulded and dried, forms the solid support of the invention. For example, if the solid support comprises gypsum plaster, the solid support precursor will comprise powdered gypsum plaster.

Preferably, the solid support precursor is present in the slurry in the amount of from about 20 to about 85 wt. %, more preferably from about 30 to about 80 wt. %, most preferably from about 50 to about 75 wt. %, based on the total weight of the slurry.

Preferably, the water is present in the slurry in the amount of from about 10 to about 75 wt. %, more preferably from about 15 to about 50 wt. %, most preferably from about 15 to about 40 wt. %, based on the total weight of the slurry.

The volatile liquid is preferably present in the slurry in the amount of from 0.5 to about 40 wt. %, more preferably from about 1 to about 20 wt. %, even more preferably from about 2 to about 10 wt. %, and most preferably from about 4 to about 6 wt. % based on the total weight of the slurry.

It is preferred that a surfactant is also present in the slurry. The surfactant is preferably present in the slurry in the amount of from about 0.1 to about 20 wt. %, more preferably from about 0.5 to about 10 wt. %, even more preferably from about 2 to about 8 wt. %, and most preferably from about 3 to about 5 wt. %, based on the total weight of the slurry. Alternatively, the surfactant may be present in the same amount as the volatile liquid.

The surfactant may be any non-ionic, anionic, cationic or amphoteric surfactant. Examples of anionic surfactants include sulfates, sulfonates, phosphates, and carboxylates. Examples of non-ionic surfactants include polysorbates, ethoxylates, alkyoxylates, alkyl polyglycosides and fatty acid esters. Examples of cationic surfactants include quaternary ammonium salts. Examples of amphoteric surfactants include betaines and phospholipids.

Preferably, the surfactant is a non-ionic surfactant, such as a polysorbate or an ethoxylated alcohol. The surfactant may be a non-ionic surfactant having a carbon chain length of about 4 to about 20 carbon atoms, preferably from about 6 to about 16 carbon atoms, ethoxylated with between about 2 to about 50 moles of ethylene oxide, preferably from about 2 and about 20 moles of ethylene oxide.

In addition, any of the optional components listed above (e.g. a dye) may be added to the slurry. For example, a dye may be added to the slurry in the amount of from about 0.001 to about 3 wt. %, preferably from about 0.001 to about 1 wt. %, based on the total weight of the slurry.

Step (b)

In step (b) a wick is contacted with the slurry in a mould. Preferably, the slurry is poured into a mould, and the wick is inserted into said mould. The mould may be made of or at least lined with any impervious material with a smooth facing, such as steel, silicone or plastic. The mould may have an opening on one side that can be closed or fastened, or may comprise two parts that can be fastened together to contain the slurry.

The wick may be at least partially coated with the slurry in step (b). Alternatively, the wick may be completely coated with the slurry in step (b).

Preferably, the wick is porous and before being contacted with the slurry a volatile liquid is applied to the porous wick, such that step (b) comprises:

(b1) applying a volatile liquid to a porous wick and subsequently contacting the wick with the slurry in a mould.

The step of applying a volatile liquid to the wick is not essential, but it is preferred that a volatile liquid is also applied to the wick even though the slurry formed in step (a) comprises a volatile liquid.

Preferably, the volatile liquid is applied to the wick such that the wick comprises at least about 10 wt. %, preferably at least about 30 wt. %, more preferably at least about 35 wt. %, even more preferably at least about 40 wt. %, of the volatile liquid, based on the total weight of the wick and the volatile liquid.

Thus, the volatile liquid may be applied to the wick such that the wick comprises from about 10 to about 70 wt. %, preferably from about 30 to about 60 wt. %, more preferably from about 35 to about 55 wt. %, of the volatile liquid, based on the total weight of the wick and the volatile liquid.

To apply the volatile liquid to a porous wick, the porous wick may be dipped or submersed in a volatile liquid or mixture of volatile liquids for sufficient time to allow the wick to become saturated with the volatile liquid(s). For example, the wick may be dipped or submersed in the volatile liquid for from about 5 seconds to about 5 hours, preferably from about 10 seconds to about 2 hours, preferably for from about 30 seconds to about 5 minutes, more preferably for about 1 minutes. Preferably, the entire wick is dipped or submersed in the volatile liquid. Alternatively, a vacuum may be used to apply the volatile liquid to the wick.

Preferably, a volatile liquid is present in both the wick and the solid support, and therefore preferably a volatile liquid is added to the slurry in step (a) and a volatile liquid is applied to the wick in step (b). In this case, the volatile liquid in the slurry may be the same or different to the volatile liquid which is applied to the wick.

Preferably, where the wick is porous, water is applied to the wick before the wick is contacted with the slurry in the mold. Step (b) may therefore comprise:

(b1) applying water to a porous wick and subsequently contacting the wick with the slurry in a mould.

Without wishing to be bound by theory, it is believed that applying water to a porous wick allows the wick to swell before contacting the wick with the slurry, such that any excess water in the slurry does not cause swelling of the wick during the drying process, which can result in cracking of the solid support.

To apply the water to a porous wick, the porous wick may be dipped or submersed in water for sufficient time to allow the wick to become saturated with water. For example, the wick may be dipped or submersed in water for from about 1 hour to about 48 hours, preferably for from about 12 hours to about 24 hours. Preferably, the entire wick is dipped or submersed in water. Alternatively, a vacuum may be used to apply water to the wick.

Optionally, the wick may be inserted into the mould before at least partially filling the mould with slurry. In this case, the mould may be vibrated whilst the slurry is added to the mould in order to avoid air bubbles forming in the mould.

Step (c)

In step (c) the slurry is allowed to dry, generally whilst still in the mould, after which the mould is removed. Alternatively, the slurry may be partially dried within the mould, and then further dried after the mould has been removed.

The slurry will usually dry at room temperature, but to speed up the drying process it is generally preferred to heat the slurry, for example in a drying oven. Thus, step (c) may comprise heating the slurry and wick within the mould to from about 30° C. to about 50° C. for a period of from about 15 minutes to about 3 hours, preferably from about 0.5 to about 2 hours, preferably about 1 hour. Alternatively, step (c) may comprise leaving the slurry and wick in the mould to dry at room temperature (i.e. 25° C.) for about 1 to about 5 hours.

After the device is removed from the mould, it is preferred to further dry to the device for a period of from about 6 hours to about 24 hours, preferably from about 8 hours to about 14 hours. This drying step may be performed at room temperature (i.e. 25° C.), but is preferably carried out at elevated temperature, for example from about 30° C. to about 50° C. This step may be carried out in a dehumidifier.

It is preferred that the slurry is not left to dry for an extended period, in order to avoid the volatile liquid completely evaporating before the dried device is packaged.

Finally, the dried device is removed from the mould (if not done during the drying stage), and packaged in airtight packaging. Any suitable airtight packaging may be used. For example, plastic having a low gas permeability may be used as packaging for the device of the present invention, preferably biodegradable or recyclable plastic.

EXAMPLES

Example 1

Preparation of a Device of the Invention

A cylindrical rattan reed having a diameter of 3 mm and a length of 240 mm was obtained from Hollia®.

A cylindrical mould having a diameter of 6 mm (3 mm greater than that of the reeds) was used. The mould had a recessed hole in the centre of the base to locate the reed. The length of the mould was 235 mm (i.e. less than that of the reed), such that the when the reed was inserted into the mould there was sufficient protrusion from the top of the mould to support the reed in place.

The mould was made of hard plaster lined with rubber.

A slurry was formed by combining the components of Table 1 in a cylindrical mixing vessel and mixing using a paddle mixer until a uniform slurry was formed.

TABLE 1

| Component | Amount (wt. %) |
| --- | --- |
| Water | 35 |
| Neodole ® 91-8 surfactant (Shell) | 5 |
| Ocean Breeze fragrance (Quintessence Fragrances) | 5 |
| Fine casting plaster, $CaSO_4 \cdot \frac{1}{2}H_2O$ (Saint-Gobain Formula) | 55 |

A reed fragrance solution was prepared by mixing the components of Table 2, after which the reed was completely immersed in the reed fragrance solution for 5 minutes.

TABLE 2

| Component | Amount (wt. %) |
| --- | --- |
| Ocean Breeze fragrance (Quintessence Fragrances) | 75 |
| Ethanol | 25 |

The slurry was poured into the mould leaving sufficient space for the volume of the reed, after which the reed was inserted through the centre of the mould into the hole in the base and fastened in place.

The mould was then placed in an oven at 40° C. for an hour, and the mould was then removed from the oven and opened. The device was removed and allowed to cool to room temperature.

Example 2

Preparation of a Device of the Invention

A cylindrical rattan reed having a diameter of 5 mm and a length of 290 mm was obtained from Hollia®.

A cylindrical mould having a diameter of 11 mm (6 mm greater than that of the reeds) was used. The mould had a recessed hole in the centre of the base to locate the reed. The length of the mould was 280 mm (i.e. less than that of the reed), such that the when the reed was inserted into the mould there was sufficient protrusion from the top of the mould to support the reed in place.

The mould was made of polythene composite tubing with an opening along the length that was fastened together to contain the liquid.

A slurry was formed by combining the components of Table 3 in a cylindrical mixing vessel and mixing using a paddle mixer until a uniform slurry was formed.

TABLE 3

| Component | Amount (wt. %) |
| --- | --- |
| Water | 17 |
| Tween ® 20 surfactant (Croda) | 4.5 |
| Lavender fragrance (Quintessence Fragrances) | 4.5 |
| Crystacal ® R hard gypsum plaster, $CaSO_4 \cdot \frac{1}{2}H_2O$ (Saint-Gobain Formula) | 74 |

A reed fragrance solution was prepared by mixing the components of Table 4, after which the reed was completely immersed in the reed fragrance solution for 5 minutes.

TABLE 4

| Component | Amount (wt. %) |
| --- | --- |
| Lavender fragrance (Quintessence Fragrances) | 50 |
| Dipropylene glycol monomethyl ether (Dowanol ® DPM-Dow Chemicals) | 50 |

The slurry was poured into the mould leaving sufficient space for the volume of the reed, after which the reed was inserted through the centre of the mould into the hole in the base and fastened in place.

The mould was then placed in an oven at 40° C. for an hour, and the mould was then removed from the oven and opened. The device was removed and further dried for 15 minutes then allowed to cool to room temperature.

Example 3

Preparation of a Device of the Invention

Three bamboo rods having a diameter of 1.3 mm and length 250 mm were obtained from Yantai Zhitong Bamboo Products Co Ltd.

A cylindrical mould with a diameter of 10 mm (8.2 mm greater than that of the rods packed tightly together) was used. The mould had three recessed holes equilaterally spaced 0.75 mm from the centre of the base to locate the rods. The length of the mould was 240 mm (i.e. less than that of the rods), such that when the rods were inserted into the mould there was sufficient protrusion from the top of the mould to hold the rods in place.

The mould was made with hard plaster lined with rubber.

The rods were completely immersed in Rose Fragrance (Quintessence Fragrances) for 4 hours.

A slurry was formed by combining the components of Table 5 in a cylindrical mixing vessel and mixed using a paddle mixer until a uniform slurry was formed.

TABLE 5

| Component | Amount (wt. %) |
| --- | --- |
| Water | 30 |
| Croduret 40 surfactant (Croda) | 5 |
| Rose Fragrance (Quintessence Fragrances) | 11 |
| Sensasperse red AS-CFB pigment dispersion (Saville Whittle) | 2 |
| Crystical R hard gypsum plaster, $CaSO_4 \cdot \frac{1}{2}H_2O$ (Saint-Gobain Formula) | 20.8 |
| Fine caster powder, $CaSO_4 \cdot \frac{1}{2}H_2O$ (Saint-Gobain Formula) | 31.2 |

The slurry was poured into the mould leaving sufficient space for the volume of the rods, after which the rods were inserted into the mould into the holes in the base and fastened in place.

The mould was then placed into an oven at 35° C. for an hour, and the mould was then removed from the oven and opened. The device was then placed back into the oven at 35° C. for a further 5 hours.

Example 4

Preparation of a Device of the Invention

A hollow aluminium tube of external diameter 6 mm (internal diameter 4 mm) and length 270 mm was obtained from Aluminium Warehouse.

A cylindrical mould with a diameter of 11 mm (5 mm greater than that of the tube) was used. The mould had a recessed hole at the centre of the base to locate the tube. The length of the mould was 250 mm (i.e. less than that of the tube), such that when the tube was inserted into the mould there was sufficient protrusion from the top of the mould to hold the tube in place.

The mould was made with hard plaster lined with rubber.

The slurry was formed by combining the components of Table 6 in a cylindrical mixing vessel and mixed using a paddle mixer until a uniform slurry was formed.

TABLE 6

| Component | Amount (wt. %) |
|---|---|
| Water | 32 |
| Croduret 40 surfactant (Croda) | 5 |
| Tropical Fragrance (Quintessence Fragrances) | 9 |
| Senasperse Green AS-GNC pigment dispersion (Saville Whittle) | 2 |
| Crystical R hard gypsum plaster, $CaSO_4 \cdot 1/2H_2O$ (Saint-Gobain Formula) | 20.8 |
| Fine caster powder, $CaSO_4 \cdot 1/2H_2O$ (Saint-Gobain Formula) | 31.2 |

The slurry was poured into the mould leaving sufficient space for the volume of the tube, after which the tube was inserted into the centre of the mould into the hole in the base and fastened in place.

The mould was then placed into an oven at 35° C. for an hour, and the mould was then removed from the oven and opened. The device was then placed back into the oven for a further 5 hours.

Example 5

Preparation of a Device of the Invention

A candle of diameter 20 mm and length 200 mm was made using wax from Sasol Wax GmbH with a wick obtained from Westdeutsche Dochtfabrik coloured with dye from bekro chemie GmbH and fragranced with 5% Rose Fragrance from Quintessence Fragrances.

A cylindrical mould with a diameter of 40 mm (20 mm greater than that of the candle) was used. The mould had a 5 mm recessed hole in the centre of the base to locate the candle. The length of the mould was 195 mm (i.e. less than that of the candle), such that when the candle was inserted into the recess it was level with the top of the mould.

The mould was made with hard plaster lined with rubber.

The slurry was formed by combining the components of Table 7 in a cylindrical mixing vessel and mixed using a paddle mixer until a uniform slurry was formed.

TABLE 7

| Component | Amount (wt. %) |
|---|---|
| Water | 33 |
| Croduret 40 surfactant (Croda) | 5 |
| Rose Fragrance (Quintessence Fragrances) | 8 |
| Sensasperse red AS-CFB pigment dispersion (Saville Whittle) | 2 |
| Crystical R hard gypsum plaster, $CaSO_4 \cdot 1/2H_2O$ (Saint-Gobain Formula) | 20.8 |
| Fine caster powder, $CaSO_4 \cdot 1/2H_2O$ (Saint-Gobain Formula) | 31.2 |

The candle was inserted into the recess in the centre of the mould and the slurry was poured into the mould until it was level with the top. The mould was gently vibrated during filling to avoid causing air bubbles.

The mould was then placed into an oven at 35° C. for an hour, and the mould was then removed from the oven and opened. The device was then placed back into the oven for a further 5 hours.

The invention claimed is:

1. A device for dispersing a volatile liquid comprising:
   a wick;
   a solid support; and
   a volatile liquid;
   wherein the wick is attached to the solid support;
   wherein the solid support is porous;
   wherein the volatile liquid is contained within pores in the solid support; and
   wherein at least about 70 wt % of the volatile liquid present in the device is contained within the solid support.

2. The device of claim 1, wherein the solid support comprises a porous inorganic material.

3. The device of claim 1, wherein the solid support comprises a porous plaster.

4. The device of claim 1, wherein the wick is porous.

5. The device of claim 4, wherein the volatile liquid is contained within pores in the wick and the solid support.

6. The device of claim 1, wherein the wick comprises a metal; a metal alloy; a plastic; wax; wood or other cellulose derivatives; a fibrous material; sponge; foam rubber; pumice; larva rock; charcoal; felt; or combinations thereof.

7. The device of claim 1, wherein the wick comprises polyester, polyethylene, cotton, sponge, foam rubber, pumice, larva rock, charcoal, felt, wood or other cellulose derivatives, or combinations thereof.

8. The device of claim 1, wherein the wick comprises bamboo, rattan or combinations thereof.

9. The device of claim 1, wherein the volatile liquid comprises a fragrance, a deodorizer, a sanitizer, an insect repellent, a pheromone, or a combination thereof.

10. The device of claim 1, wherein at least about 40% of the total surface of the wick is attached to the solid support.

11. The device of claim 1, wherein the solid support at least partially encapsulates the wick.

12. The device of claim 1, wherein the volatile liquid is contained within the wick and/or solid support in the amount of from about 5 to about 60 wt. %, based on the total weight of the device.

13. The device of claim 1, wherein the volatile liquid is present in the wick in the amount of from about 20 to about 60 wt. % based on the total weight of the wick and the volatile liquid, and/or wherein the volatile liquid is contained within the solid support in the amount of from about 1 to about 40 wt. %, based on the total weight of the solid support and the volatile liquid.

14. The device of claim 1, wherein the device does not comprise an external reservoir.

15. The device of claim 1, wherein the volatile liquid is contained solely within the wick and/or the solid support.

16. The device of claim 1, wherein the solid support comprises an additive selected from a dye, an odour eliminator, glitter, a metallic power, an antioxidant, a UV inhibitor, or combinations thereof.

17. The device of claim 1, further comprising airtight packaging.

18. The device of claim 1, wherein the solid support fully encapsulates the wick.

* * * * *